United States Patent
Teders et al.

(10) Patent No.: US 8,125,309 B2
(45) Date of Patent: Feb. 28, 2012

(54) FAIL-SAFE REMOTE CONTROL

(75) Inventors: Matthias Teders, Hamburg (DE); Gerhard Hornfeldt, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1116 days.

(21) Appl. No.: 11/916,542

(22) PCT Filed: Jun. 1, 2006

(86) PCT No.: PCT/IB2006/051762
§ 371 (c)(1),
(2), (4) Date: Dec. 5, 2007

(87) PCT Pub. No.: WO2006/131862
PCT Pub. Date: Dec. 14, 2006

(65) Prior Publication Data
US 2010/0134315 A1    Jun. 3, 2010

(30) Foreign Application Priority Data
Jun. 7, 2005   (EP) .................................. 05104915

(51) Int. Cl.
G05B 23/02    (2006.01)
(52) U.S. Cl. .................. 340/3.43; 340/508; 340/825.16; 340/825.69; 714/31; 318/638
(58) Field of Classification Search ............... 340/12.1, 340/12.22, 12.3, 12.31, 12.5, 13.1, 13.2, 340/13.22, 13.25, 680, 522, 507, 825.71–77; 307/112
See application file for complete search history.

(56) References Cited

U.S. PATENT DOCUMENTS

| | | | | |
|---|---|---|---|---|
| 4,304,001 A | * | 12/1981 | Cope | 714/4.4 |
| 4,435,862 A | * | 3/1984 | King et al. | 5/611 |
| 4,649,469 A | * | 3/1987 | Gabillet | 700/1 |
| 4,724,554 A | * | 2/1988 | Kowalski et al. | 5/610 |
| 4,956,592 A | * | 9/1990 | Schulte et al. | 318/560 |
| 5,235,258 A | | 8/1993 | Schuerch | |
| 5,359,515 A | * | 10/1994 | Weller et al. | 701/45 |
| 5,377,109 A | * | 12/1994 | Baker et al. | 701/14 |
| 5,544,376 A | * | 8/1996 | Fromson | 5/618 |
| 5,600,214 A | * | 2/1997 | Fromson | 318/120 |
| 6,177,734 B1 | * | 1/2001 | Masberg et al. | 290/31 |
| 6,201,481 B1 | * | 3/2001 | Bellingroth | 340/680 |
| 6,206,416 B1 | * | 3/2001 | Faigle et al. | 280/735 |
| 6,255,944 B1 | * | 7/2001 | Addy | 340/539.3 |
| 6,396,224 B1 | | 5/2002 | Luff et al. | |
| 6,995,682 B1 | * | 2/2006 | Chen et al. | 340/12.22 |
| 7,014,000 B2 | * | 3/2006 | Kummer et al. | 180/19.3 |
| 7,127,371 B2 | * | 10/2006 | Duckert et al. | 702/179 |
| 7,319,406 B2 | * | 1/2008 | Vazach et al. | 340/679 |
| 7,505,754 B2 | * | 3/2009 | Kazmierczak et al. | 455/404.1 |
| 7,703,158 B2 | * | 4/2010 | Wilker et al. | 5/616 |
| 7,784,127 B2 | * | 8/2010 | Kuro et al. | 5/601 |
| 2002/0167399 A1 | * | 11/2002 | Enders et al. | 340/438 |

FOREIGN PATENT DOCUMENTS

| | | |
|---|---|---|
| DE | 10026263 A1 | 3/2001 |
| EP | 0999533 A2 | 5/2000 |
| WO | WO0217846 A1 | 3/2002 |
| WO | WO02078589 | 10/2002 |

* cited by examiner

*Primary Examiner* — Daniel Wu
*Assistant Examiner* — Muhammad Adnan

(57) ABSTRACT

The present invention relates to a remote control (160) operates fail-safe. The remote control comprises a safety filter (150) in order to provide a fail save operation. The present invention also relates to an adjustable patient table (100) comprising a fail-safe wireless remote control for controlling an actuator to adjust the table.

21 Claims, 2 Drawing Sheets

FAIL-SAFE REMOTE CONTROL

FIELD OF THE INVENTION

The present invention relates to a fail-safe interface for in an environment with strict safety requirements.

The present invention also relates to a remote control that requires a fail-safe interface.

The present invention is particularly relevant for a wireless remote control that can control movements of in a patient table in a medical environment but can be used in any system where adjustments of articles need to be made while safety concerns due to erroneous conditions are high. Such an environment includes a hospital operation and investigation room, which have adjustable patient tables for use with a wide variety of equipment such as X-ray machines, MRI scanners etc.

BACKGROUND OF THE INVENTION

In 2000, IEC accepted the IEC 61508 standard ("Functional Safety of Electrical/Electronic/Programmable Electronic Safety-Related System") to support companies that use Safety Instrumented Systems (SIS) to protect persons and facilities from hazardous events. Four safety integrity levels (SIL, level 1~4) are defined by IEC 61508 to statistically represent the integrity of the SIS when a process demand occurs. The SIL takes into account device integrity, architecture, voting, diagnostics, systematic and common cause failures, testing, operation, and maintenance. A SIL establishes an order of magnitude targets for risk reduction. This target failure measure is the intended probability of dangerous mode failures to be achieved in respect of the safety integrity requirements, specified in terms of either the average probability of failure to perform the safety function on demand (for a low demand of operation); or the probability of a dangerous failure per hour (for a high demand or continuous mode of operation). The higher the SIL, the greater the impact of a failure and therefore the lower the failure rate that is acceptable. The method used to derive the SIL designation, must be carefully documented using well-established methods. The first step to determine or designate a SIL, is to conduct a process hazards analysis (PHA). The methodology of IEC 61508 focuses most of the actual evaluation on the potential injury, fatality, or other risk to individual persons.

In an environment where articles need to be adjusted using a wired or wireless remote control, actuators may be used switched by relays. Especially when the articles comprise hospital patient table, safety concerns take a high priority.

In a typical embodiment, a micro-controller scans the inputs of a keyboard of a wireless remote control and/or a footswitch that is used to control a movable patient table. When a person controls the remote an output of its microprocessor will control a relay. Typically, a micro-controller in a remote control could get in an error situation. When an output would get stuck the patient table could then move uncontrollable something that can be very dangerous and must be prevented.

When a micro-controller is connected to a relay an error analysis is difficult to perform as semiconductors and software are involved. For this reason an error or a fault condition is not always detectable. In case of safety relevant applications, this is a serious problem. When an error condition would occur however, it is desirable that any movement will stop immediately to prevent any damage, or worse, patient harm.

It is also desirable to use components in a fail-safe system that are known from the past and that have a well known (reliable) behaviour.

SUMMARY OF THE INVENTION

It is, accordingly, an object of the present invention to provide a safety interface for a remote control.

It is another object of the invention to provide the safety filter for the remote control to adjust a patient table that will cause any movement to halt in case an error condition has been detected.

In one embodiment, a micro-controller is controlling a relay using a safety filter.

In another embodiment, the safety filter comprises a band-filter that outputs a relay control activation signal only when the micro-controller outputs a signal with a main component that lies within a certain frequency range. In a preferred embodiment, the safety filter comprises a transformer that is known from the past to be reliable enough to be used in fail-safe systems.

In another embodiment present invention provides an adjustable patient table (100) comprising a fail-safe wireless remote control for controlling an actuator to adjust the table.

In a preferred embodiment the invention provides a remote control (160) for controlling a safety relevant function. It comprises a first user input signal path and a second user input signal path, a transmitter (110) for transmitting a first signal from the first signal path and a second signal from the second signal path, a receiver (120) for receiving the first signal and the second signal, a first switch control that in response of a validated first signal can output a first switch control output signal, a second switch control comprising a safety filter (150) that in response of a validated second signal can output a second switch control output signal. The safety relevant function can only be activated when the first switch control outputs a validated first switch control output signal and the safety filter outputs a validated second switch control output signal.

These and other aspects of the invention will be apparent from and will be elucidated with reference to the embodiments described hereinafter.

DESCRIPTION OF THE DRAWINGS

The present invention will now be described in more detail, by way of example, with reference to the accompanying drawings, wherein.

Throughout the drawings, the same reference numeral refers to the same element, or an element that performs substantially the same function.

DETAILED DESCRIPTION OF THE INVENTION

Figure 1:
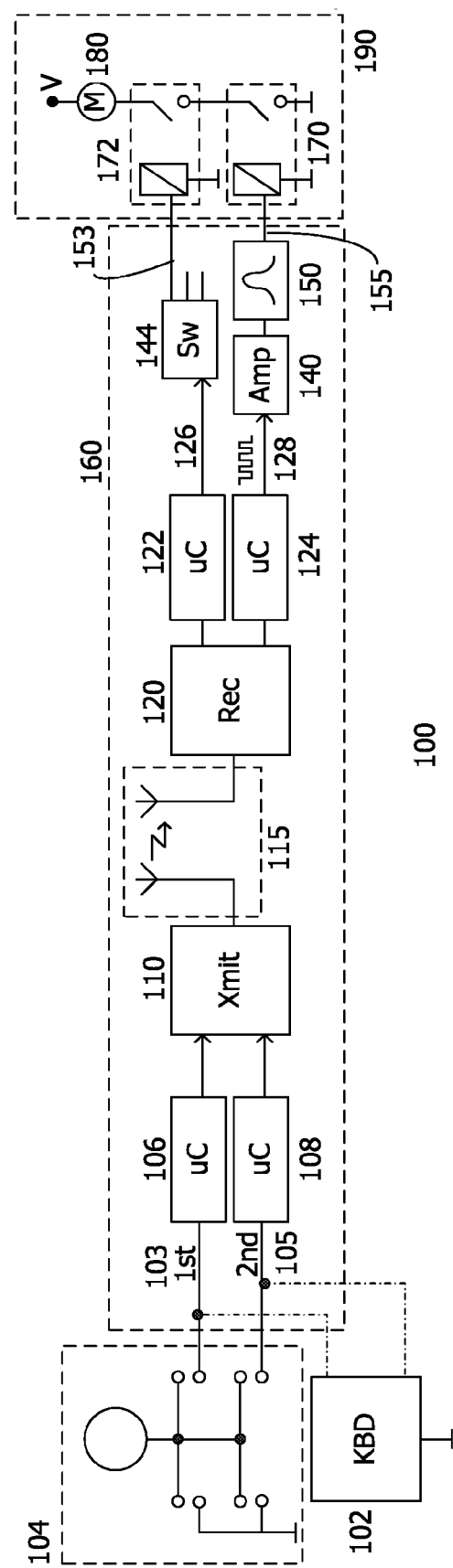
FIG. 1 shows a block-diagram of a remote control system 160 in a safety relevant system 100 in accordance with the invention.

FIG. 1 shows a block-diagram of a remote control system 160 in a safety relevant system 100 in accordance with the invention. System 100 comprises a keyboard scanner 102, a footswitch 104 (with open contacts on off-state), remote control system 160, and safety relevant device 190. Remote control system 160 comprises a dual executed and redundant signal path (visualized as $1^{st}$ 103 and $2^{nd}$ 105) and comprises microcontroller 106, 108, 122, 124, transmitter 110, transmission path 115, receiver 120, relay switch driver 144, amplifier 140 and safety filter 150. Device 190 comprises relays 170 and 172 and motor 180. Motor 180 can only be activated when both relays 170 and 172 are activated. Relay 170 can only be activated with a validated first switch control signal 153 and relay 172 can only be activated with a validated second switch control signal 155.

An example of device 190 is a patient table that can, e.g., be moved up and down using motor 180 as part of an actuator. However any movement will abruptly be stopped when system 100 would get into an error condition by at least deactivating relay 170 or relay 172, which would otherwise pose a hazardous situation for, e.g., a patient lying on the table.

To safely control a function in the safety relevant system 100, a control line is typically be executed double, the second being redundant to the first one. This starts with footswitch 104 and keyboard 102 that have two outputs lines per function. Microcontrollers 106 and 108 check the integrity of the signal on $1^{st}$ 103 and the signal on $2^{nd}$ 105 and they check each other status as well. In case of any fault condition, microcontroller will not output a signal that could effect an action. Another task of microcontrollers 106 and 108 is to prepare their respective input signals for transmission my transmitter 110. Receiver 120 will receive a multiplex of the transmitted signals and will separate them in respective output signals to microcontrollers 122 and 124. Transmission path 115 can be wireless (e.g., radio frequent, RF), infra-red (IR), or cable conducted (e.g., with the $1^{st}$ and the $2^{nd}$ signal modulated on one and the same conducting carrier). Microcontrollers 122 and 124 will check the integrity of each respective input signal and will check each other on a fault condition as well (by preferably a handshake). If again no error condition has been detected microcontroller 122 will output a first control signal 126 for relay switch driver 144. Also if again no error condition has been detected microcontroller 122 will output a second control signal 128 to amplifier 140. Second control signal 128 comprises a periodic pulse train signal (with a block form shape) with a ground frequency component between F1 and F2, typically F0. The idea is that when microcontroller would be in an error condition, it would not be able to output such a, typically software generated, block form shaped signal. F1 will be larger than 0 Hz and F2 will be smaller than the tact frequency of microcontroller 124.

The pulse train signal will be used to control relay 170. But before the pulse train reaches the relay it will pass amplifier 140 followed by (preferably narrow band) filter 150 Amplifier may be needed as the signal 128 coming from microcontroller 124 will typically not be powerful enough to drive relay 170 after passing filter 150. This band-pass filter only will output a substantial signal when the pulse-train has a main frequency component that matches the band-pass filter (so with F1<frequency<F2).

Figure 2:
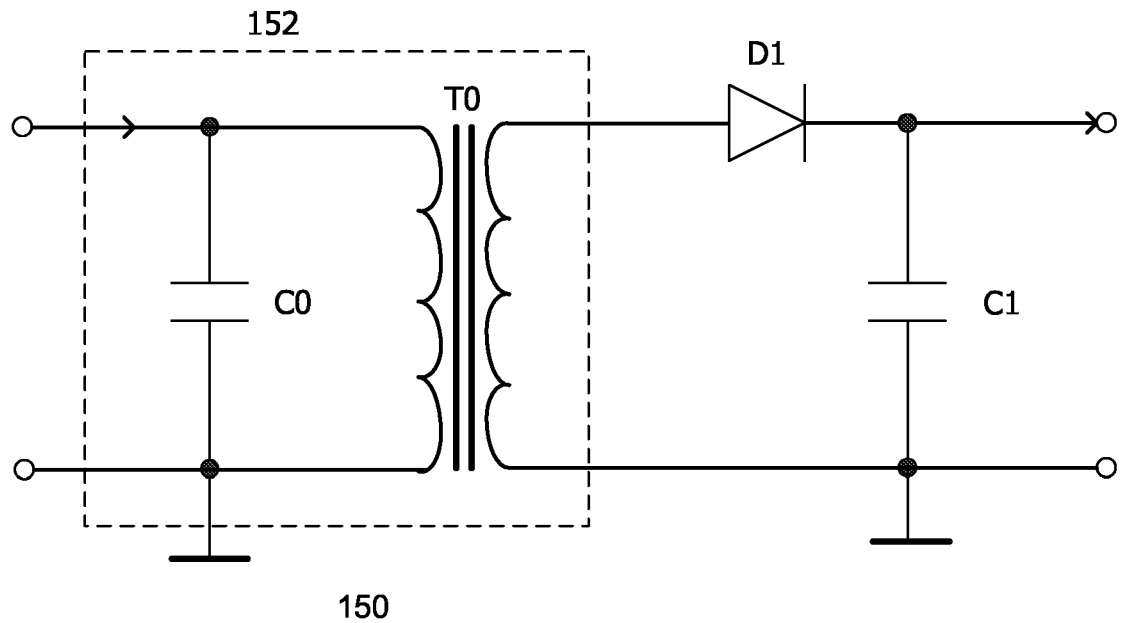
FIG. 2 shows a best mode implementation of a safety filter 150 for use in the remote control system 100 in a safety relevant system 100 in accordance with the invention.

FIG. 2 shows a best mode implementation of a safety filter 150 for use in the remote control system 100 in a safety relevant system 100 in accordance with the invention Filter 150 includes LC Band pass filter 152 comprising capacitor C0 and transformer T0, rectifier diode D1 and capacitor C1. In active operation filter 150 will receive a block wave signal that will be band-pass filtered by a selection transformer comprising capacitor C0 and transformer T0 and then substantially rectified by diode D1 and capacitor C1. The resulting DC-output signal will be powerful enough to close the switch by driving relay 170.

Figure 3:
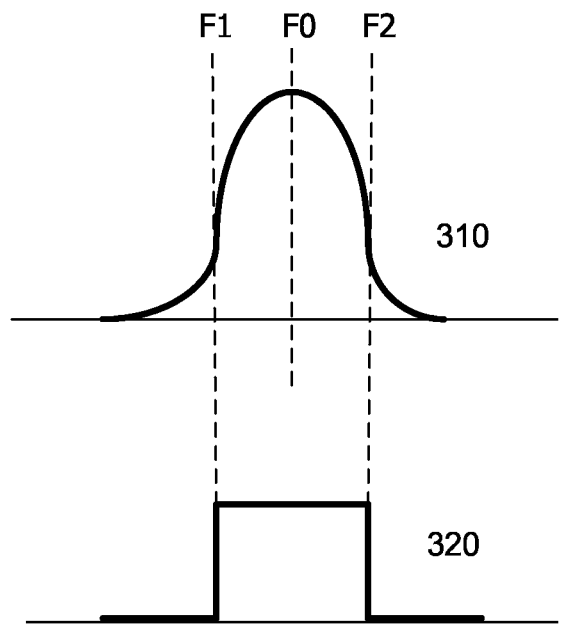
FIG. 3 shows the frequency response of safety filter 150 and the relay 170 sensitivity with respect to the safety filter response in accordance of a best mode embodiment in accordance with the invention.

FIG. 3 shows the frequency response 310 of safety filter 150 and the relay 170 sensitivity 320 with respect to the safety filter response in accordance of a best mode embodiment in accordance with the invention. LC Band pass filter 152 acts as a narrow band filter with a characteristic as in 310. When a pulse train with a main frequency component with F1<frequency<F2 is offered to filter 150 a DC signal will appear at the output of filter 150 that is large enough to activate relay switch 170. The filter rectifies the filtered pulse train by means of D1 and C1. In case of an error condition (Software error or hardware error within the micro-controller), the dedicated frequency will not be transmitted by microcontroller 124.

No Signal of a conspicuously higher or lower frequency than F0 will substantially pass the (band-) filter and will not activate relay 170. Components C0, T0, D1, and C1 should be chosen carefully and known to be highly reliable and predictable. As these components are passive, the number of error conditions that need to be taken into account for failure analysis is much limited and thus an operation in compliance with safety standards such as IEC 61508 can be realized.

To ensure a most reliable fail-safe operation, all components used in system 100 should be chosen to be reliable and simple For that reason it is recommended to use as much as possible well-known and tested components. As the behavior of all these components is known, all error cases can be analyzed and simulated in the design phase.

The fail-safe wired or wireless remote control is very useful in a medical setting where cables can be hazardous and make operation of medical equipment awkward. The remote control can for instance be used for controlling movements of a patient table. That can for instance be useful when maneuvering the table to an medical system for examining a patient who is lying on the table. The remote control may well be used for controlling a vertical/horizontal movement of the patient table with a remote control in such a system the remote control can be applied in a much wider area of use where safety concerns play a role.

One of ordinary skill in the art will recognize that alternative schemes can be devised to create a fail-safe remote control by making tweaks in the control and/or system described. For instance, pre-programmed state machines could replace microcontrollers 106, 108, 122 and 124. Instead of controlling a motor, also other functions could be switches using relays 170 and 172, such as activating an exposure of an X-ray machine or activating (or de-activating) any other function which use has safety regulations.

The foregoing merely illustrates the principles of the invention. It will thus be appreciated that those skilled in the art will be able to devise various arrangements which, although not explicitly described or shown herein, embody the principles of the invention and are thus within its spirit and scope.

For instance a multiple of independent footswitches and/or keyboard signal could be connected to microcontrollers 106 and 108 for controlling different (e.g., safety related) functions. Consequently microcontrollers 122 and 124 could output a multiple of signals for controlling the different functions. Per function a different safety filter 150 could be devised with a different pass band behavior.

The invention claimed is:

1. An interface for a safety relevant function, said interface comprising:
a first switch control configured for: a) receiving a first signal representative of a command inputted for remotely controlling said function; b) detecting, based on said first signal, whether an error condition exists; and c) only if no error condition is detected by said first switch control, outputting a first switch control signal, said first switch control signal for activating said function provided a second switch control signal is outputted; and a second switch control comprising a safety filter, and configured for: a) receiving a second signal representative of said command; b) detecting, based on said second signal, whether an error condition exists; and c) only if no error condition is detected by said second switch control, outputting, by said safety filter, said second switch control signal, said second switch control signal for activating said function provided said first switch control signal is outputted.

2. The interface of claim 1, further configured for coupling said first switch control signal to a first switch for controlling said function, and for coupling said second switch control to a second switch for controlling said function, said safety filter comprising a band-pass filter that comprises a transformer.

3. The interface of claim 2, wherein at least one of said first switch and said second switch comprises a relay.

4. A safety relevant system including the interface of claim 1, said system further comprising:
a device comprising a motor configured for activation, by said interface, only when said function is activated by said interface.

5. The safety relevant system of claim 4, further comprising:
a wireless remote control into which the inputting of said command occurs.

6. A safety relevant system including:
a device comprising a motor for adjusting said device; and
the interface of claim 2 for enabling an operator, via inputting of said command, to adjust the device to a targeted state,
said motor configured for being activated, by said interface, only when said first switch control signal activates said first switch and said second switch control signal activates said second switch.

7. The safety relevant system of claim 6 wherein at least one of the first and the second switch comprises a relay.

8. The safety relevant system of claim 7 wherein the device comprises an adjustable patient table.

9. The safety relevant system of claim 6, further comprising a wireless remote control into which the inputting of said command occurs.

10. The interface of claim 1, further comprising:
a receiver for receiving said first signal, and said second signal, to be received by the first and second switch controls, respectively.

11. The interface of claim 10, said receiver being configured for wireless reception of said first signal and of said second signal.

12. A remote control comprising the interface of claim 10, said remote control for controlling said function and further comprising:
a first input signal path, and a second input signal path, for receiving said command; and
a transmitter for transmitting said first signal from said first input signal path, and said second signal from said second input signal path, for receipt by said receiver.

13. A remote control comprising the interface of claim 12, said remote control for controlling said function and further comprising:
a pair of redundant control lines respectively comprising the first and second input signal paths.

14. The remote control of claim 13, further comprising processors respectively on said control lines, said processors configured for respectively checking integrity of said first and said second signals, and for selectively, based on a result of said checking, supplying them to said transmitter.

15. The remote control of claim 12, configured for forming the signal applied to said safety filter as a block form shaped signal.

16. The interface of claim 1, said first switch control, and said second switch control, each being further configured for performing their respective outputting to a safety relevant device in which said function is implemented.

17. The interface of claim 1, said first signal not being applied to a safety filter.

18. The interface of claim 1, said first signal not being applied to a safety filter comprising a band-pass filter and a transformer.

19. The interface of claim 1, said outputting by the first and second switch controls being performed in real time response to the inputting of said command.

20. A method for interfacing a safety relevant function for remote control, said method comprising:
detecting, based on a received first signal, whether an error condition exists, said first signal representative of a command inputted for remotely controlling said function;
only if no error condition is detected by said first switch control, outputting a first switch control signal, said first switch control signal for activating said function provided a second switch control signal is outputted;
detecting, based on a received second signal, whether an error condition exists, said second signal representative of said command; and,
only if no error condition is detected by said second switch control, outputting, by a safety filter, said second switch control signal, said second switch control signal for activating said function provided said first switch control signal is outputted.

21. One or more non-transitory, computer-readable media, in which respective computer programs for interfacing a safety relevant function for remote control are stored which, when executed by one or more corresponding processors, cause said one or more processors to carry out a plurality of steps, among said plurality being the steps of:
detecting, based on a received first signal, whether an error condition exists, said first signal representative of a command inputted for remotely controlling said function;
only if no error condition is detected by said first switch control, outputting a first switch control signal, said first switch control signal for activating said function provided a second switch control signal is outputted;
detecting, based on a received second signal, whether an error condition exists, said second signal representative of said command; and,
only if no error condition is detected by said second switch control, outputting, by a safety filter, said second switch control signal, said second switch control signal for activating said function provided said first switch control signal is outputted.

* * * * *